(12) United States Patent
Levy

(10) Patent No.: US 8,813,752 B2
(45) Date of Patent: *Aug. 26, 2014

(54) SECRETING CONDOM

(76) Inventor: Linda Levy, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/585,404

(22) Filed: Aug. 14, 2012

(65) Prior Publication Data

US 2012/0305004 A1 Dec. 6, 2012

Related U.S. Application Data

(63) Continuation-in-part of application No. 12/893,571, filed on Sep. 29, 2010.

(51) Int. Cl.
| | | |
|---|---|---|
| A41D 19/00 | (2006.01) | |
| A61F 5/44 | (2006.01) | |
| A61F 6/02 | (2006.01) | |
| A61F 6/04 | (2006.01) | |
| B05D 3/00 | (2006.01) | |

(52) U.S. Cl.
USPC ........... 128/844; 128/842; 128/917; 128/918; 427/2.3; 604/327; 604/346; 604/347; 604/348; 604/349

(58) Field of Classification Search
USPC ............. 128/842, 844, 917, 918; 600/38–41; 604/347–352; 206/69; 427/2.3
See application file for complete search history.

(56) References Cited

U.S. PATENT DOCUMENTS

| | | |
|---|---|---|
| 2,410,460 A | 11/1946 | Robinson |
| 4,332,243 A | 6/1982 | Gutnick |
| 4,917,113 A | 4/1990 | Conway |
| 4,919,149 A | 4/1990 | Stang |
| 5,102,405 A | 4/1992 | Conway |
| 5,205,298 A | 4/1993 | Hurst |
| 5,318,043 A | 6/1994 | Burr et al. |
| 5,327,775 A | 7/1994 | Epshetsky |
| 5,513,652 A | 5/1996 | Schwartz |
| 5,640,973 A | 6/1997 | Blinn |
| 5,669,869 A | 9/1997 | Strom |
| 5,896,983 A | 4/1999 | Wood |
| 6,098,626 A | 8/2000 | Kim |
| 6,536,438 B1 | 3/2003 | Kakonyi |
| 7,654,265 B2 | 2/2010 | Attlia |

(Continued)

FOREIGN PATENT DOCUMENTS

| | | | |
|---|---|---|---|
| JP | 07015013 U | * 3/1995 | ............... A61F 6/04 |
| WO | WO 89/01768 | 3/1989 | |
| WO | WO 2010/020996 | 2/2010 | |

Primary Examiner — Patricia Bianco
Assistant Examiner — Brandon L Jackson
(74) Attorney, Agent, or Firm — Mayback & Hoffman, P.A.; Gregory L. Mayback; Rebecca A. Tie

(57) ABSTRACT

A male contraceptive device includes a condom-like sheath that is placed over the male genital member and has a flavor-infusing agent disposed within the distal end. The distal end is operable to release, eject, or secrete the flavor-altered semen during male ejaculation. The condom-like sheath is shaped to elastically conform to the elongated shape of a male genital member. The sheath has an open proximal end for receiving the male genital member and the distal end has a distal tip that is selectively closed. The distal tip defines a reservoir containing the flavor-infusing agent and is operable, upon pressure of seminal fluid entering the reservoir, to cause the flavor profile or characteristic of the seminal fluid to be altered and to permit the release of the seminal fluid that has entered the reservoir.

16 Claims, 3 Drawing Sheets

(56) References Cited

U.S. PATENT DOCUMENTS

| | | |
|---|---|---|
| 7,963,285 B2 | 6/2011 | Attila |
| 2005/0133041 A1 | 6/2005 | Tune |
| 2006/0048784 A1 | 3/2006 | Turner |
| 2007/0017528 A1 | 1/2007 | Osterberg |
| 2007/0175484 A1 | 8/2007 | Staab |
| 2009/0107513 A1 | 4/2009 | Zedalis et al. |

* cited by examiner

SECRETING CONDOM

CROSS-REFERENCE TO RELATED APPLICATIONS

This application is a continuation-in-part application of U.S. patent application Ser. No. 12/893,571, filed on Sep. 29, 2010, the entire disclosure of which is hereby incorporated herein by reference in its entirety.

FIELD OF INVENTION

The present invention lies in the field of male contraceptive devices. More specifically, the present disclosure relates to a condom-like sheath that is placed over the male genital member and has a flavor-infusing agent disposed inside the selectively closed, distal end of the condom-like sheath whereby the distal end is operable to release, eject, or secrete the resulting favor-infused fluid during male ejaculation.

BACKGROUND OF THE INVENTION

A large variety of condom types are known in the art. In general, condoms are used as one type of contraceptive tool to reduce the possibility of transmitting diseases and unwanted pregnancy between sexual partners. Over time, condoms have evolved in their construction to take into consideration the comfort and sensation that is provided to the user and others who are engaged in the sexual activity. For example, the materials used to construct condoms are generally hypoallergenic and nonabrasive, and oftentimes, are lubricated by some type of fluid composition to prevent the occurrence of an allergic reaction, rash, or other frictional discomfort that is caused by the necessary tight and elastic fit of the condom. In addition, the materials are chosen to reduce the thickness of the condom wall while still maintaining the safety of the device in order to alleviate the symptomatic problem of limited sensation. The condom has also been used as a way to actually enhance or heighten sexual stimulation by incorporating textured elements on the interior and/or exterior surface of the condom that come into intimate contact with the skin, or by applying natural or synthetic compounds to the interior or exterior surface of the condom that have been shown to cause a sexual reaction upon contact with the skin. Thus, the condom has proven to be a useful device in enhancing the pleasure of sex.

While condoms are typically used to reduce the possibility of transmitting a sexually-transmitted disease and the risk of unwanted pregnancy during sexual intercourse, condoms are also used for practicing safe, oral-genital sex, which has gained an increasing popularity in the public eye and has become a more widely publicly-accepted form of sexual activity in comparison to prior history. Although there is no concern of pregnancy, the oral cavity and the surrounding lips and facial skin all provide a substantial opportunity for the transmission of disease through any breaks in the skin/blood barrier or mucosa when in direct, skin-to-skin contact with the genital region of a sexual partner. Accordingly, although somewhat obstructive, a condom, when placed over the male genital area, provides an important barrier between the skin and tissue surfaces of the mouth and the skin surface of the penis when performing oral-genital sex upon a male partner.

However, when involving the oral senses of the body, taste and smell are significant factors in determining whether a person has a pleasurable experience in performing oral-genital sex. Because condoms are typically all made of a natural or synthetic polymer material such as latex, rubber, polyurethane, or polyisoprene, they generally do not have an inviting odor, taste or texture when introduced into the mouth. In an effort to mask any undesirable smells or tastes of the condom or to add a unique element of interest to the sexual activity, efforts have been made to add a variety of flavorful substances to the exterior surface of the condom without harming its structural integrity. For example, ingestible or edible flavored substances have been added to lubricants that are used with condoms. In another example, thin films or coatings, or tubular elements of flavorful components have been added to the exterior surface of the condom that dissolve, react, release or otherwise break free from the condom upon frictional contact or, for example, upon contact with saliva or body heat.

Thus, although some advances using flavored substances have been made to make condoms less offensive in their odor and taste in consideration of oral-genital sexual activity, these flavored substances are only applied, either manually or during manufacture, to the exterior surface of the condom as that is the only surface of the condom that comes into contact with the oral cavity. Historically, condoms are sealed and closed at the distal end to prevent the secretion of any bodily fluids. As such, the flavored additions being made to condoms do not address any adverse or hindering odors or smells of any bodily fluids that may be secreted during oral-genital sex that does not involve the use of a condom or in instances where the condom is removed just prior to climax. For many people, any contact with or ingestion of these bodily fluids creates a significant aversion to engaging in oral-genital sex or performing oral-genital sex for any significant period of time or until the male achieves a climax. Particularly, the odor and smell of seminal fluid is oftentimes considered undesirable by a person who is performing oral-genital sex upon a male partner. Therefore, it would be beneficial to equip the interior of a condom-like device with a flavor-infusing agent that improves the taste and smell of any seminal fluid that is secreted from the penis so as not to hinder the pleasure and completion of the act of oral-genital sex.

In furtherance of the objective set forth above, it would be advantageous that the flavor-infusing agent be disposed within the condom-like in such a manner that the flavor component substantially comingles with, or otherwise alters the flavor profile or characteristic of, the seminal fluid upon ejaculation.

Accordingly, a need exists to overcome the problems discussed above.

SUMMARY OF THE INVENTION

With the foregoing and other objects in view, there is provided, in accordance with the invention, a male contraceptive device comprising an elastic condom-like sheath defining an interior and having an open proximal end for receiving a male genital member and a distal end that is selectively closed. The distal end has a distal tip that is in fluid communication with the interior and defines a reservoir having a flavor-infusing agent disposed therein such that, upon pressure from seminal fluid entering the reservoir, the flavor of the seminal fluid is altered by the flavor-infusing agent and the altered seminal fluid is released from the distal end and into the environment outside the sheath.

In accordance with another feature of the invention, the flavor-infusing agent is an ingestible flavored compound that substantially commingles with and alters the flavor of seminal fluid entering the reservoir.

In accordance with a further feature of the invention, the flavor-infusing agent is an ingestible flavored compound that, upon contact with seminal fluid entering the reservoir, alters the flavor of the seminal fluid.

In accordance with an added feature of the invention, the flavor-infusing agent is a porous barrier that permits fluid to flow therethrough and, upon contact with seminal fluid entering the reservoir and flowing therethrough, alters the flavor of the seminal fluid.

In accordance with an additional feature of the invention, the flavor-infusing agent is at least one of a flavored liquid, a dry, flavored powder, and a flavored gas compound.

In accordance with yet another feature of the invention, the flavor-infusing agent is a flavored coating that has been applied along an interior surface of the reservoir and is operable to infuse flavor into a fluid upon contact with that fluid.

In accordance with yet a further feature of the invention, the distal end further comprises at least one perforation that, when broken, permits fluidic communication between the interior and the environment outside the sheath and release of seminal fluid from inside the reservoir into the environment.

In accordance with yet an added feature of the invention, the distal end further comprises at least one removable portion that, when removed from the distal end, creates at least one aperture in the distal end that permits fluid communication between the interior and the environment outside the sheath and release of the fluid from inside the reservoir into the environment.

In accordance with yet an additional feature of the invention, the distal tip further comprises an aperture permitting fluid communication between the interior and the environment outside the sheath.

In accordance with a concomitant feature of the invention, the interior of the sheath further comprises at least one perforation that, when broken, permits fluidic communication between the reservoir and the environment outside the sheath and release of the fluid from inside the reservoir and into the environment.

In accordance with a further feature of the invention, the interior of the sheath further comprises at least one selectively-closed aperture that permits fluidic communication between the reservoir and the environment outside the sheath and release of the fluid from inside the reservoir and into the environment.

In accordance with yet an added feature of the invention, there is provided a patch removably secured to the distal end and sealingly covering the aperture such that, when the patch is removed from the distal end, the distal tip is operable to release the fluid from the reservoir through the aperture into the environment outside the sheath.

In accordance with a further added feature of the invention, there is provided a tab removably secured to the distal end and sealingly covering the aperture such that, when the tab is at least partially removed from the distal end, the distal tip is operable to release the fluid from the reservoir through the aperture into the environment outside the sheath.

In accordance with an additional feature of the invention, the distal end further comprises a one-way valve that, when biased open, creates an aperture in the distal end that permits the release of fluid in a single direction from the reservoir through the aperture into the environment outside the sheath.

In accordance with a further feature of the invention, the one-way valve is operable to bias open in response to force created by seminal fluid entering the reservoir.

With the objects of the invention in view, there is also provided a method for constructing a male contraceptive device, comprising forming an elastic condom-like sheath to define a sheath interior and to have an open proximal end for receiving a male genital member and a selectively closed distal end with a distal tip in fluid communication with the sheath interior and defining a reservoir; disposing a flavor-infusing agent within the reservoir, the flavor-infusing agent being operable to, upon mixture with seminal fluid entering the reservoir, alter the flavor of the seminal fluid; and wherein the selectively closed distal end is operable to release the altered seminal fluid from the distal end into the environment outside the sheath in response to pressure from the seminal fluid entering the reservoir.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims. The construction and method of operation of the invention, however, together with additional objects and advantages thereof, will be best understood from the following description of specific embodiments when read in connection with the accompanying drawings.

Although the invention is illustrated and described herein as embodied in a condom-like sheath that is placed over the male genital member and has a flavorful formulated solution disposed inside the closed, distal tip of the condom-like sheath, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims.

BRIEF DESCRIPTION OF THE DRAWINGS

Advantages of embodiments of the present invention will be apparent from the following detailed description of the preferred embodiments thereof, which description should be considered in conjunction with the accompanying drawings in which.

DETAILED DESCRIPTION OF THE INVENTION

Figure 1:
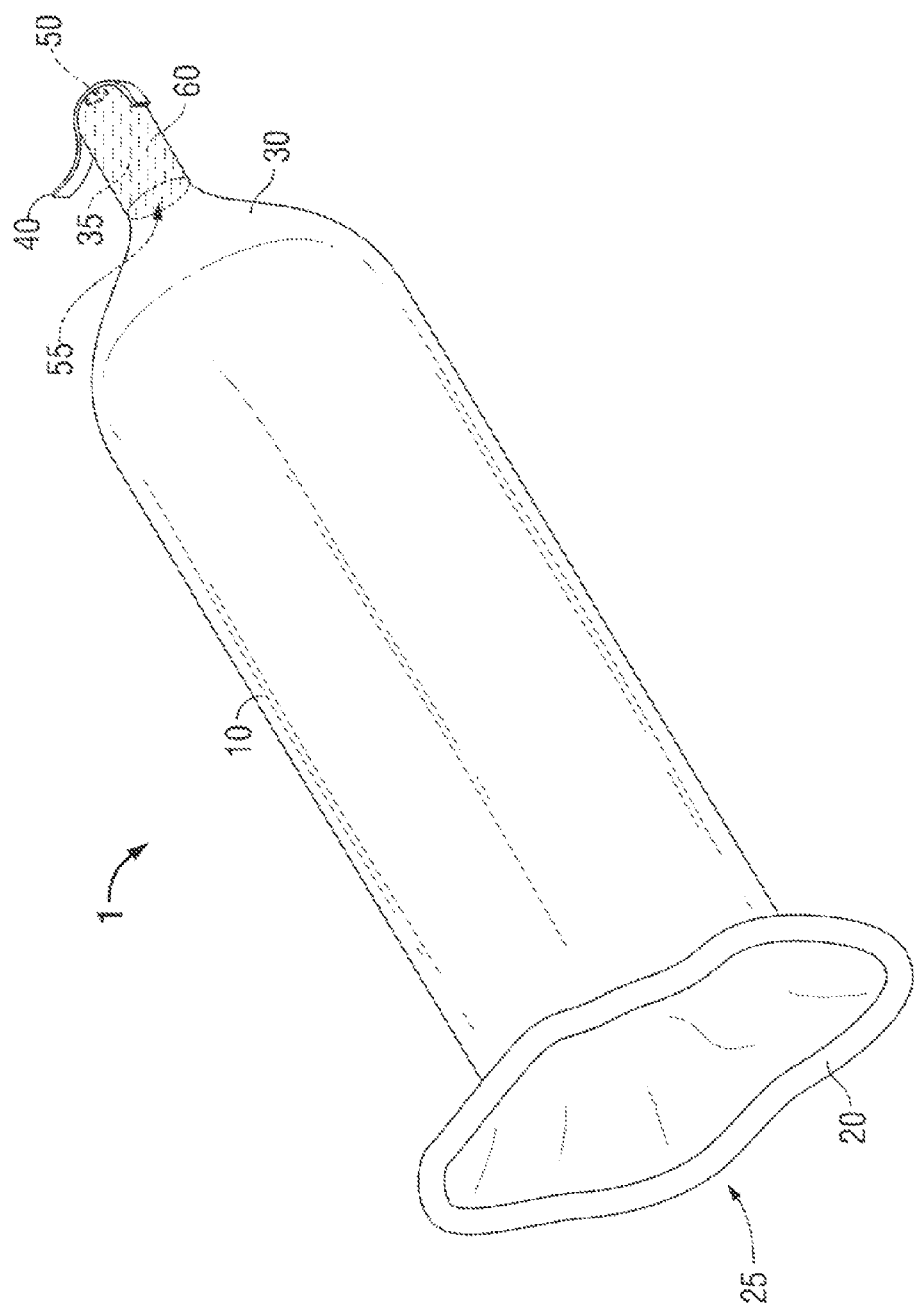
FIG. 1 is a perspective view from a side of a condom-like sheath device according to a first exemplary embodiment of the present invention, the dashed lines in the proximal end indicating a stretched contour of the proximal end.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the object being described.

The device of the present invention provides a unique way to flavorfully alter the odor and taste of semen or other seminal fluid that is secreted or ejaculated by a male partner while engaging in oral-genital sex. The objective of the present invention is to improve the experience of coming into contact with or ingesting the semen or other seminal fluid by the partner who is performing the oral activity on the male partner and to add an unexpected and interesting element to the sexual act.

Referring now to the figures of the drawings in detail and first, particularly to FIG. 1, there is shown a first exemplary embodiment of the condom-like sheath device according to the present invention. The device 1 is comprised of a longitudinal tubular member 10 that has a proximal end 20 and a tapered distal end 30. The longitudinal tubular member 10 is shaped to elastically conform to the elongated shape of a male genital member so as to prevent the inadvertent removal of the device 1 during sexual activity. The proximal end 20 provides an opening 25 that allows the male genital member (not shown) to be inserted into the device 1 such that the device 1 acts as a sheath that tightly covers the male genital member, when erect, in a condom-like fashion. The longitudinal tubular member 10 of the device 1 may be comprised of any suitable material for making condoms, such as natural or synthetically-made latex, as is well-known in the art. The opening 25 is shown in FIG. 1 as being extended or stretched outward from its at-rest state of the device 1, the dashed lines in the proximal end indicating a stretched contour of the opening 25.

In the present embodiment, the distal end 30 of the device 1 is provided with and terminates into a distal tip 35 that forms a reservoir 55. As shown in FIG. 1, inside the reservoir 55 there is disposed a flavor-infusing agent 60 (indicated with darkened lines). The flavor-infusing agent 60 may be comprised of any non-toxic compound, or a combination of compounds, that is both edible and capable of commingling with, or otherwise altering the flavor profile or characteristic of, seminal fluid that has come into contact with the flavor-infusing agent 60 inside the reservoir 55. Such agents include, but are not limited to, flavored liquid substances, flavored gaseous compounds, or dry, flavored coatings, powders, or chemical films disposed inside or along the interior surface of the reservoir 55. Such agents may be in the form of, for example, flavored nectars, syrups, gels, or extracts, flavored, dry powders such as cocoa or mint powders, plain crystalline sugar or sugar infused with other flavors (e.g. vanilla), a flavor-infused vapor, and flavored liquids that have been applied as a film or coating on the interior surface of the reservoir and either remain in liquid form or are allowed to dry (similar to the ingestible breath freshener films currently available on the market that dissolve on contact with the tongue). In another example, a small mesh material or other type of porous or filter-like surface or barrier that imparts a flavor upon any substance that flows through it may be positioned inside the reservoir 55. The flavor of the flavor-infusing agent 60 may be chosen from an extensive variety of flavors that include, but are not limited to, the flavor of any type of fruit, spice, mint, or candy. The flavor-infusing agent may be disposed within the reservoir 55 during the method of manufacture and assembly of the device 1, or, alternatively, may be disposed within the reservoir 55 just prior to use of the device 1.

Unlike existing condom devices, the distal end 30 of the device 1 is atypically made to not be completely or permanently closed. For example, as shown in the exemplary embodiment of FIG. 1, the distal tip 35 may include a small aperture 50 that allows fluid to leak from the reservoir 55 of the distal tip 35, as is described in further detail below. In another exemplary embodiment, the distal tip 35 may be formed to have a perforated portion (not shown) that can be torn along the perforations, and in some cases, removed, to selectively create the small aperture 50. In the first example, whereby the distal tip 35 is initially formed with a small aperture 50, the small aperture 50 may be selectively sealed by a patch or tab 40 that is removably secured to the distal end 30 or the distal tip 35 such that it may be torn off at a later time when it is desirable to release or dispense the flavored solution 60 from the device 1. The patch or tab 40 may be removably secured to the distal end 30 or the distal tip 35 by any suitable method that does not damage the exterior surface of the distal end 30 or the distal tip 35 and does not unduly hamper the sexual activity. For example, the patch or tab 40 may be removably secured to the distal end 30 or the distal tip 35 by a non-toxic and, if desired, edible pressure sensitive adhesive or a contact adhesive that is applied to the bonding surfaces of both the distal end 30 or the distal tip 35 and the patch or tab 40. The above-described embodiments are merely exemplary and it is envisioned that there are a variety of ways, other than a single small aperture at the distal tip, in which the device 1 may be made to not be completely or permanently closed such that the contents of the reservoir may be secreted or exit the device 1 during use. For example, a number of perforated areas and/or selectively sealed apertures may be formed in a number of places along the distal end 30 of the device 1, or elsewhere along the length of the longitudinal tubular member 10 of the device 1. It is also envisioned that a system or series of one or more ducts (not shown) that are in fluid communication with the reservoir 55 may be formed in the interior of the device 1. Upon pressure build-up in the reservoir 55, the ducts funnel or otherwise direct the contents of the reservoir 55 to another area of the device 1 for secretion.

In operation, the condom-like sheath device 1 is applied to the male genital member in a condom-like fashion prior to engaging in sexual intercourse or oral-genital sex, whereby the fluid-infusing agent 60 has been disposed within the reservoir 55. Initially, the structural measures for selectively sealing the distal end 30 are kept in place. For example, with respect to the embodiment of FIG. 1, any perforations at the distal tip 35 are kept intact or, where used, the patch or tab 40 is removably secured to the distal tip 35. As the sexual activity progresses, the perforations are broken or the patch or tab 40 is torn off or otherwise removed from the distal tip 35 at a desirable point in time, such as the instant before the male reaches climax. Breaking of the perforations or removal of the patch or tab 40 creates or opens the small aperture 50. By opening the small aperture 50 at that point in time, the ejaculate released by the male during climax substantially comingles or comes into contact with the flavor-infusing agent 60. Due to the force of the ejaculation, the flavor profile or characteristic of the seminal fluid is influenced by the flavor-infusing agent 60, and the resulting fluid is dispensed or secreted from the distal tip 35. As a result, any encounter by others with the seminal fluid is much less offensive in odor and taste due to the flavored additive.

Figure 2:
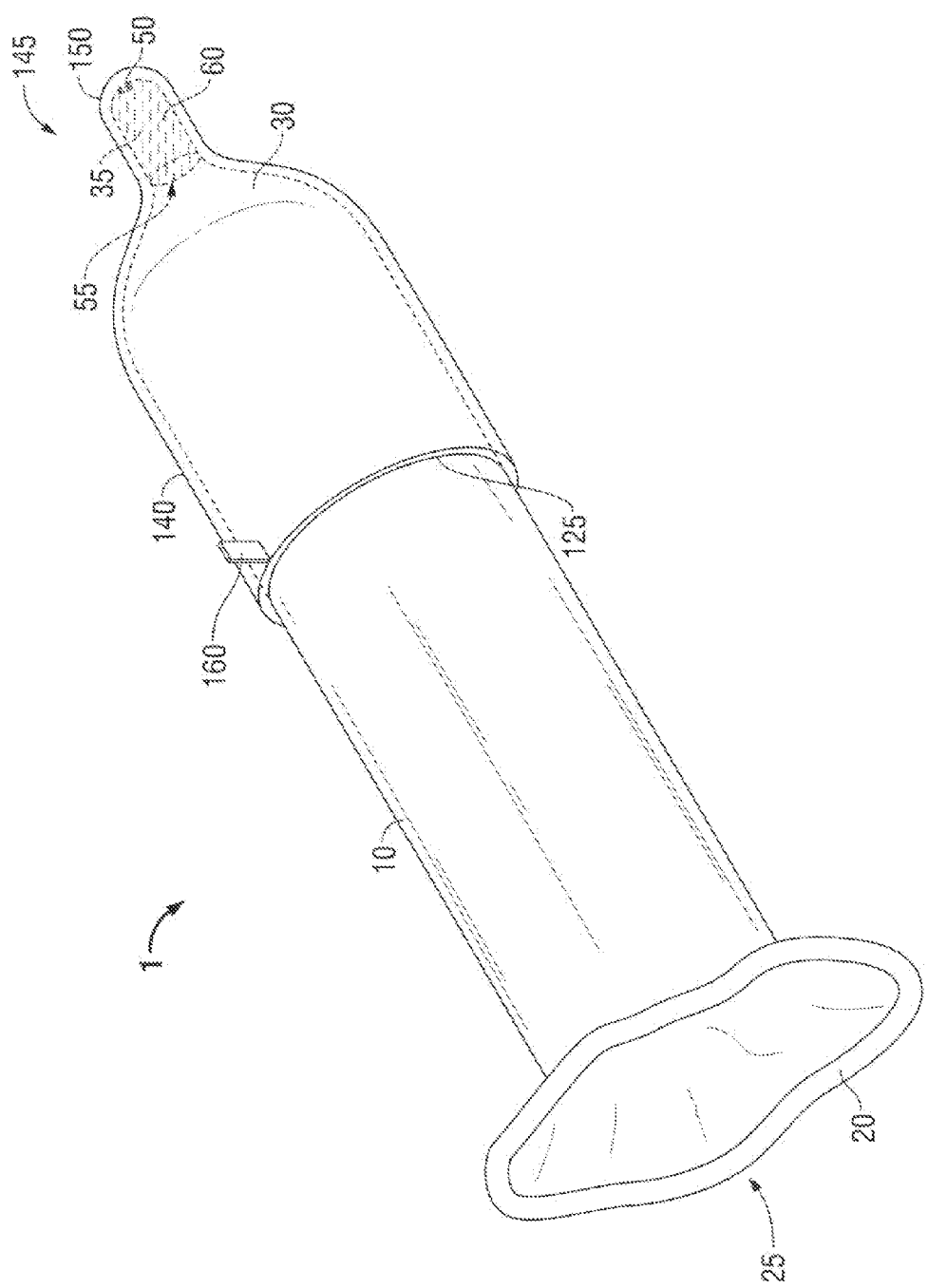
FIG. 2 is a perspective view from a side of a condom-like sheath device according to a second exemplary embodiment of the present invention, the dashed lines in the proximal end indicating a stretched contour of the proximal end.

In FIG. 2, there is shown another exemplary embodiment of the condom-like sheath device 1. Similar to the exemplary embodiment depicted in FIG. 1, the device 1 is comprised of a longitudinal tubular member 10, having a proximal end 20 and a tapered distal end 30 and shaped to elastically conform to the elongated shape of a male genital member. The proximal end 20 provides an opening 25 for insertion of the male genital member such that the device 1 acts as a sheath that tightly covers the male genital member as described above with respect to the embodiment of FIG. 1. The opening 25 is shown in FIG. 2 as being extended or stretched outward from its at-rest state of the device 1, the dashed lines in the proximal end indicating a stretched contour of the opening 25. The distal end 30 of the device 1 terminates into distal tip 35 that forms a reservoir 55 in which there is disposed a flavor-infusing agent 60. Further, the distal tip 35 includes a small aperture 50 that allows fluid to leak from the reservoir 55.

However, in this particular embodiment, the small aperture 50 is not defined by one or more breakable perforations or is not temporarily and selectively sealed by a patch or tab that is removably secured to the distal tip 35. Rather, as is shown in FIG. 2, the small aperture 50 is selectively sealed by a second outer longitudinal tubular member 140 that is placed over the inner tubular member 10 in overlapping contact and covers at least the distal end 30 of the inner tubular member 10. The second outer tubular member 140 is shaped to tightly overlap the inner tubular member 10 so as to prevent it from being removed inadvertently. Thus, the second outer tubular member 140 may also be comprised of any material that is suitable for a condom device such that is has the necessary elasticity and, in an exemplary embodiment, the material is the same as the material of the device 1. To further prevent the inadvertent removal of the second outer tubular member 140, a non-toxic and, if desired, edible pressure sensitive adhesive or contact adhesive may be applied between the contact surfaces of the inner tubular member 10 and the outer tubular member 140 to temporarily hold the inner tubular member 10 and the outer tubular member 140 together.

In a similar manner to the inner tubular member 10, the second outer tubular member 140 has an open proximal end 125 that allows it to be slipped over at least the distal end 30 of the inner tubular member 10. A distal end 145 of the second outer tubular member 140 terminates into a permanently closed distal tip 150 that forms a reservoir 155. For purposes of the present invention, the term "closed" includes, but is not limited to an impervious barrier. For example, the term "closed" may, in some embodiments, be defined as meaning "water impermeable." Reservoir 155 is shaped to receive the reservoir 55 of the distal tip 35 of the inner tubular member 10 when the second outer tubular member 140 is slipped over the inner tubular member 10. Accordingly, the small aperture 50 of the inner tubular member 10 is sealed by the overlapping, closed distal tip 150 of the second outer tubular member 140.

As described above, at a chosen point in time during sexual intercourse or oral-genital sex, it may be desirable to unseal the small aperture 50 to allow fluids to leak from the distal tip 35. This is accomplished by pulling off or otherwise removing the second outer tubular member 140 and leaving the inner tubular member 10 completely exposed. By unsealing the small aperture 50 at that point in time, the force of the ejaculate released by the male during climax causes the seminal fluid to substantially comingle or come into contact with the flavor-infusing agent 60 and to be dispensed or secreted from the distal tip 35 with an altered flavor profile or characteristic. As one exemplary embodiment for assisting with removal of the second outer tubular member 140 from the inner tubular member 10, one or more tabs 160 can be located at the second outer tubular member 140 and the tabs 160 can be attached to the second outer tubular member 140 or integral therewith.

Figure 3:
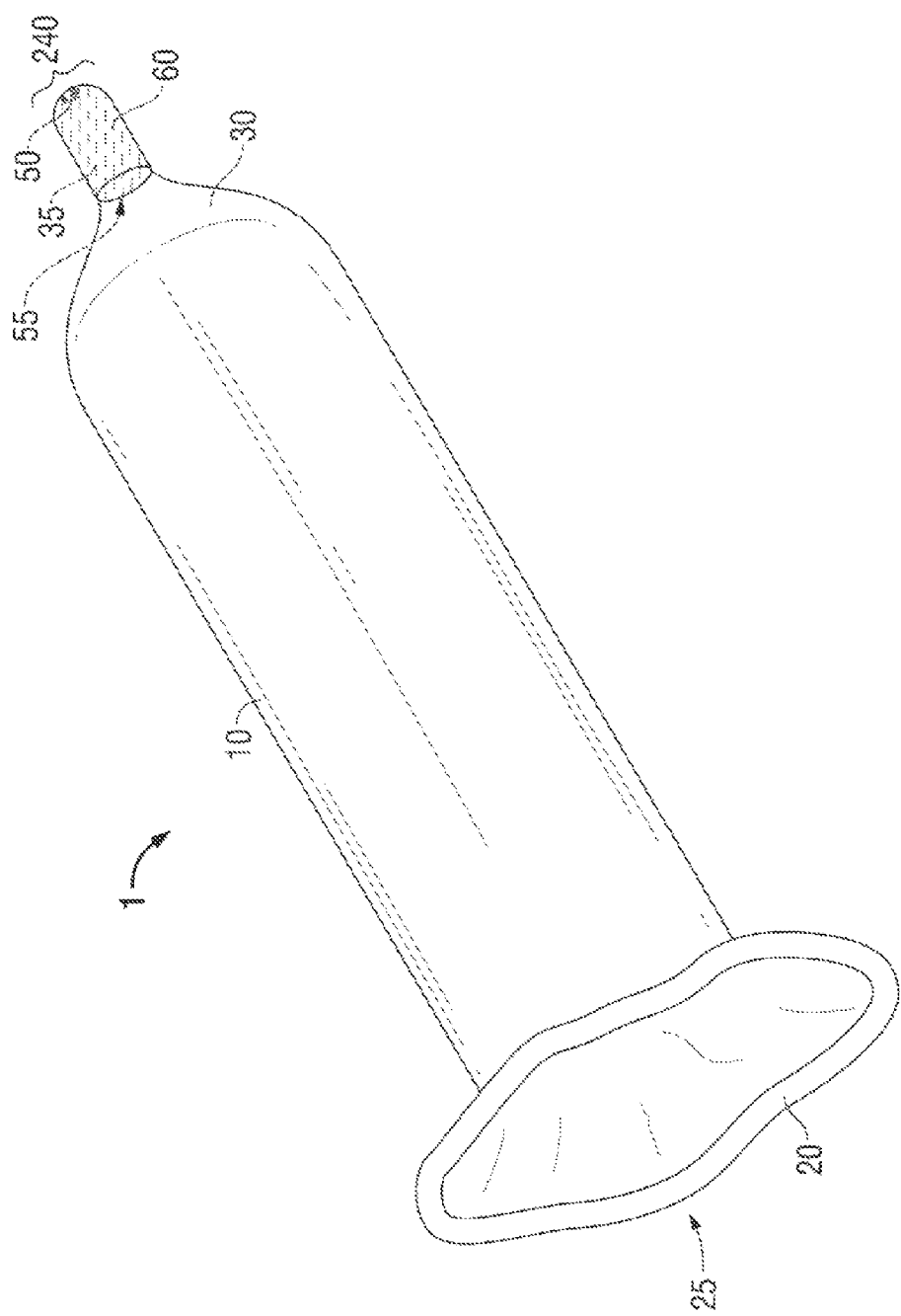
FIG. 3 is a perspective view from a side of the condom-like sheath device according to a third exemplary embodiment of the present invention, the dashed lines in the proximal end indicating a stretched contour of the proximal end.

Referring now to FIG. 3, there is shown another exemplary embodiment of the condom-like sheath device 1. Similar to the exemplary embodiments depicted in FIGS. 1 and 2, the device 1 is comprised of a longitudinal tubular member 10, having a proximal end 20 and a tapered distal end 30 and shaped to elastically conform to the elongated shape of a male genital member. The proximal end 20 provides an opening 25 for insertion of the male genital member such that the device 1 acts as a sheath that tightly covers the male genital member as described above with respect to the embodiments of FIGS. 1 and 2. The opening 25 is shown in FIG. 3 as being extended or stretched outward from its at-rest state of the device 1, the dashed lines in the proximal end indicating a stretched contour of the opening 25.

The distal end 30 of the device 1 terminates into a distal tip 35 that forms a reservoir 55 in which there is disposed a flavor-infusing agent 60. The distal tip 35 has a small aperture 50 that allows fluid to leak from the reservoir 55 through a one-way valve 240 that is integral with the distal tip 35 and permits fluid to exit, but not enter, the reservoir 55 in only one direction. Examples of a suitable one-way valve include, but are not limited to, a check valve, a flap valve and/or a slit valve.

The one-way valve 240 is operable to open when the amount of pressure or force inside the reservoir 55 reaches a certain point that is sufficient to bias the one-way valve open. In this particular embodiment, the one-way valve 240 is configured to open in response to the natural pressure that is created during male ejaculation. Thus, in operation, the ejaculate released by the male during climax causes the one-way valve 240 to open, thereby causing the semen to combine with or come into contact with the flavor-infusing agent 60 and to exit the device 1 through the aperture 50 at substantially the same time.

To further the intensity of the flavor of the device 1, flavorful elements may be applied to or integrated into the exterior surface of the device 1, as is well-known in the art.

In addition, to provide a visual indication of the flavor of the flavor-infusing agent 60 that is disposed inside the reservoir 55 of the distal tip 35, artistic embellishments may be applied to the exterior surface of the device 1 to enhance or create a theme that is consistent or associated with the particular flavor of the agent 60.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A male contraceptive device, comprising:
an elastic condom-like sheath defining an interior and having:
an open proximal end for receiving a male genital member; and
a distal end that is selectively closed and has a distal tip that:
is in fluid communication with the interior; and
defines a reservoir having a flavor-infusing agent disposed therein such that, upon pressure from seminal fluid entering the reservoir upon ejaculation, the flavor of the seminal fluid is altered by the flavor-infusing agent and the altered seminal fluid is released from the distal end and into the environment outside the sheath.

2. The device according to claim 1, wherein the flavor-infusing agent is an ingestible flavored compound that substantially commingles with and alters the flavor of seminal fluid entering the reservoir.

3. The device according to claim 2, wherein the flavor-infusing agent is at least one of:
a flavored liquid;
a dry, flavored powder; and
a flavored gas compound.

4. The device according to claim 1, wherein the flavor-infusing agent is an ingestible flavored compound that, upon contact with seminal fluid entering the reservoir, alters the flavor of the seminal fluid.

5. The device according to claim 4, wherein the flavor-infusing agent is a flavored coating that has been applied along an interior surface of the reservoir and is operable to infuse flavor into a fluid upon contact with that fluid.

6. The device according to claim 1, wherein the distal tip further comprises an aperture permitting fluid communication between the interior and the environment outside the sheath.

7. The device according to claim 6, further comprising a patch removably secured to the distal end and sealingly covering the aperture such that, when the patch is removed from the distal end, the distal tip is operable to release the fluid from the reservoir through the aperture into the environment outside the sheath.

8. The device according to claim 6, further comprising a tab removably secured to the distal end and sealingly covering the aperture such that, when the tab is at least partially removed from the distal end, the distal tip is operable to release the fluid from the reservoir through the aperture into the environment outside the sheath.

9. The device according to claim 1, wherein the distal end further comprises a one-way valve that, when biased open, creates an aperture in the distal end that permits the release of fluid in a single direction from the reservoir through the aperture into the environment outside the sheath.

10. The device according to claim 9, wherein the one-way valve is operable to bias open in response to force created by seminal fluid entering the reservoir.

11. The device according to claim 1, wherein the flavor-infusing agent is a porous barrier that permits fluid to flow therethrough and, upon contact with seminal fluid entering the reservoir and flowing therethrough, alters the flavor of the seminal fluid.

12. The device according to claim 1, wherein the distal end further comprises at least one perforation that, when broken, permits fluidic communication between the interior and the environment outside the sheath and release of seminal fluid from inside the reservoir into the environment.

13. The device according to claim 1, wherein the distal end further comprises at least one removable portion that, when removed from the distal end, creates at least one aperture in the distal end that permits fluid communication between the interior and the environment outside the sheath and release of the fluid from inside the reservoir into the environment.

14. The device according to claim 1, wherein the interior of the sheath further comprises at least one perforation that, when broken, permits fluidic communication between the reservoir and the environment outside the sheath and release of the fluid from inside the reservoir and into the environment.

15. The device according to claim 1, wherein the interior of the sheath further comprises at least one selectively-closed aperture that permits fluidic communication between the reservoir and the environment outside the sheath and release of the fluid from inside the reservoir and into the environment.

16. A method for constructing a male contraceptive device, comprising:
forming an elastic condom-like sheath to define a sheath interior and to have:
an open proximal end for receiving a male genital member; and
a selectively closed distal end with a distal tip in fluid communication with the sheath interior and defining a reservoir;
disposing a flavor-infusing agent within the reservoir, the flavor-infusing agent being operable to, upon mixture with seminal fluid entering the reservoir, alter the flavor of the seminal fluid; and
wherein the selectively closed distal end is operable to release the altered seminal fluid from the distal end into the environment outside the sheath in response to pressure from the seminal fluid entering the reservoir upon ejaculation.

* * * * *